(12) United States Patent
Matsushita et al.

(10) Patent No.: US 6,320,655 B1
(45) Date of Patent: Nov. 20, 2001

(54) DEFECT-POSITION IDENTIFYING METHOD FOR SEMICONDUCTOR SUBSTRATE

(75) Inventors: Hiroshi Matsushita, Funabashi; Norihiko Tsuchiya, Tokyo-To; Youko Toyomaru, Yokohama, all of (JP)

(73) Assignee: Kabushiki Kaisha Toshiba, Kawasaki (JP)

(*) Notice: Subject to any disclaimer, the term of this patent is extended or adjusted under 35 U.S.C. 154(b) by 0 days.

(21) Appl. No.: 09/525,943

(22) Filed: Mar. 15, 2000

(30) Foreign Application Priority Data

Mar. 16, 1999 (JP) .................................................. 11-070433

(51) Int. Cl.⁷ .................................................. G01N 21/00
(52) U.S. Cl. .................................... 356/237.2; 356/237.5; 356/614; 356/72
(58) Field of Search .................................. 356/614, 620, 356/239.8, 237.2, 237.3, 237.4, 237.5, 72

(56) References Cited

U.S. PATENT DOCUMENTS

| | | | |
|---|---|---|---|
| 5,267,017 | * 11/1993 | Uritsky et al. | 356/237 |
| 5,847,821 | 12/1998 | Tracy et al. | 356/237 |
| 5,877,035 | 3/1999 | Fujino et al. | 438/16 |
| 5,917,588 | * 6/1999 | Addiego | 356/237 |
| 6,028,664 | * 2/2000 | Cheng et al. | 356/237.4 |

* cited by examiner

*Primary Examiner*—Hoa Q. Pham
*Assistant Examiner*—Roy M Punnoose
(74) *Attorney, Agent, or Firm*—Oblon, Spivak, McClelland, Maier & Neustadt, P.C.

(57) ABSTRACT

A defect-position identifying method for a semiconductor substrate comprises the steps of: forming at least three reference points on a semiconductor substrate; detecting the reference points and a defect on the semiconductor substrate by means of a first evaluating system, which is provided for evaluating the defect on the semiconductor substrate, to measure coordinate values of the reference points and the defect in a system of coordinates of the first evaluating system; detecting the reference points on the semiconductor substrate by means of a second evaluating system, which is provided for evaluating the defect on the semiconductor substrate, to measure coordinate values of the reference points in a system of coordinates of the second evaluating system; determining an affine transformation for transforming the system of coordinates of the first evaluating system to the system of coordinates of the second evaluating system on the basis of the coordinate values of each of the reference points in the first and second evaluating systems; and identifying the position of the defect in the system of coordinates of the second evaluating system on the basis of the determined affine transformation and the coordinate values of the defect in the system of coordinates of the first evaluating system. Thus, it is possible to precisely identify the position of the defect.

13 Claims, 12 Drawing Sheets

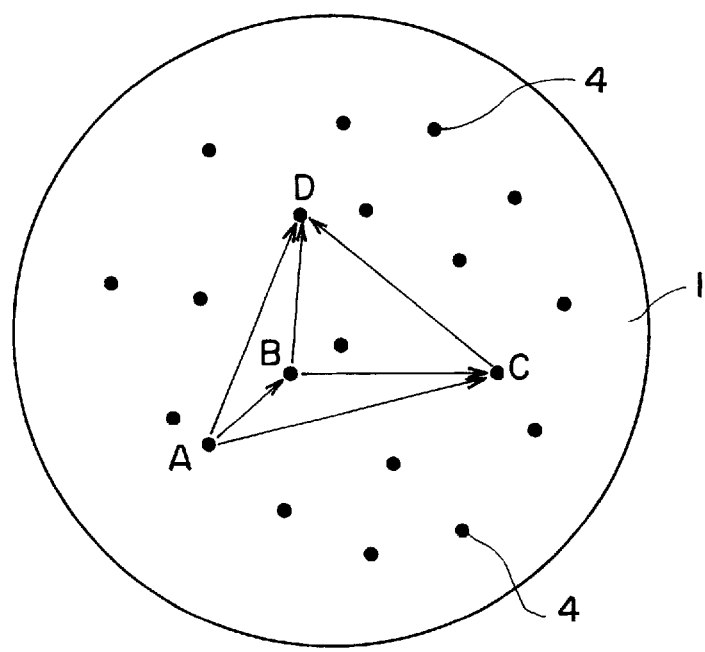
F I G. 12
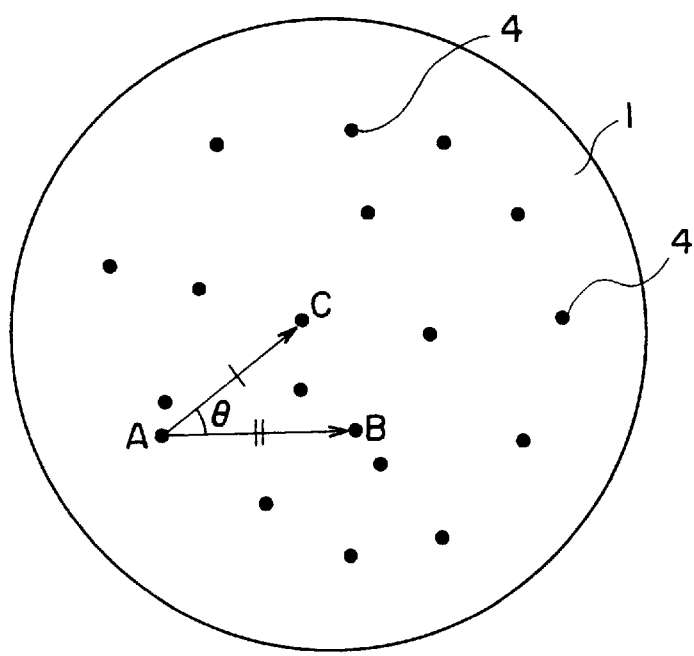
F I G. 14

| EVALUATED AREA / DEPTH POSITION | SURFACE | BELOW SURFACE |
|---|---|---|
| WHOLE SURFACE (MACRO) | PARTICLE COUNTER | VISIBLE SCATTERING TOPOGRAPHY |
| STEREOSCOPIC ANALYSIS (MICRO) | AFM | SCM, CROSS-SECTION TEM |

FIG.16 ived from the macroscopically catching system and the microscopically catching system.

DEFECT-POSITION IDENTIFYING METHOD FOR SEMICONDUCTOR SUBSTRATE

BACKGROUND OF THE INVENTION

1. Field of the Invention

The present invention relates generally to a defect-position identifying method for a semiconductor substrate.

2. Description of the Related Art

With the high density integration of ULSIs, zero defects in the surface layer of a semiconductor substrate serving as an element active layer are required. It is generally known that defects due to pull-up, called on grown-in defects, exist in the crystal of a semiconductor substrate which is obtained by slicing and polishing a single crystalline silicon pulled up from a crucible. These defects have only a density of about $10^6$ cm$^{-}$ detected mainly by light scattering. Therefore, it is very difficult to carry out the direct observation by means of a transmission electron microscope (which will be also hereinafter referred to as a "TEM") or an atomic force microscope (which will be also hereinafter referred to as an "AFM"), and the substance thereof did not clear until recent years.

However, it was succeeded in 1995 to observe defects themselves in a gate oxide film by means of a TEM by utilizing the copper's property of being selectively deposited on defect existing places, and it was revealed that most of these defects comprised voids.

In general, systems for evaluating a semiconductor substrate having defects are classified into two kinds of systems, i.e., systems for macroscopically catching the presence of defects, and systems for microscopically catching the presence of defects. The macroscopically catching systems are classified into two kinds of systems, i.e., systems for catching defects on the surface of a semiconductor substrate (e.g., a particle counter), and systems for catching defects directly below the surface of a semiconductor substrate (e.g., a visible light scattering topography), as shown in FIG. 16. The microscopically catching systems are classified into two kinds of systems, i.e., systems for catching defects on the surface of a semiconductor substrate (e.g., AFM), and systems for capturing defects directly below the surface of a semiconductor substrate (e.g., a scanning capacitance microscope (which will be also hereinafter referred to as a "SCM") and a cross-section TEM), as shown in FIG. 16. Furthermore, although the SCM originally carries out an evaluating method for obtaining a two-dimensional distribution of the density of dopant (impurity) in a semiconductor element, the SCM can also be used for evaluating defects below the surface, which can not be observed by the AFM.

In order to identify the position of a defect, it is general to evaluate the defect by a microscopically catching system after evaluating the defect by a macroscopically catching system. It is therefore important to deliver coordinate values indicative of the position of the defect between the macroscopically catching system and the microscopically catching system.

Conventionally, the coordinate values of the defect have been measured by using the X-Y stage of each of systems, on which a semiconductor substrate is mounted, and the shape of the semiconductor substrate (a circumference and an orientation flat or notch).

However, there is a limit to the mechanical precision of the stage, and the shape of the semiconductor substrate has errors during working. Therefore, even if a defect is found by the macroscopically capturing system, the defect does not always come within the range of the microscopically catching system, so that there is a problem in that the position of the defect can not be identified.

SUMMARY OF THE INVENTION

It is therefore an object of the present invention to eliminate the aforementioned problems and to provide a defect-position identifying method for a semiconductor substrate, which is capable of precisely identifying the position of a defect.

In order to accomplish the aforementioned and other objects, according to a first aspect of the present invention, there is provided a defect-position identifying method for a semiconductor substrate comprising the steps of: forming at least three reference points on a semiconductor substrate; detecting the reference points and a defect on the semiconductor substrate by means of a first evaluating system, which is provided for evaluating the defect on the semiconductor substrate, to measure coordinate values of the reference points and the defect in a system of coordinates of the first evaluating system; detecting the reference points on the semiconductor substrate by means of a second evaluating system, which is provided for evaluating the defect on the semiconductor substrate, to measure coordinate values of the reference points in a system of coordinates of the second evaluating system; determining an affine transformation for transforming the system of coordinates of the first evaluating system to the system of coordinates of the second evaluating system on the basis of the coordinate values of each of the reference points in the first and second evaluating systems; and identifying the position of the defect in the system of coordinates of the second evaluating system on the basis of the determined affine transformation and the coordinate values of the defect in the system of coordinates of the first evaluating system.

The first evaluating system may be a particle counter, and the second evaluating system may comprise an optical microscope and an atomic force microscope having a common system of coordinates to the optical microscope, the coordinate values of the reference points in the system of coordinates of the second evaluating system being measured by means of the optical microscope.

Alternatively, the first evaluating system may comprise an optical microscope and a visible light scattering topography having a common system of coordinates to the optical microscope, and the second evaluating system may comprise a focused ion beam drawing system, the coordinate values of the reference points and the defect in the system of coordinates of the first evaluating system being measured by means of the optical microscope and the visible light scattering topography.

The defect-position identifying method for a semiconductor substrate may further comprise a step of selecting an internal defect existing in the semiconductor substrate from the defects detected by means of the visible light scattering topography, and the step of identifying the position of the defect in the system of coordinates of the second evaluating system may comprise the steps of: estimating the position of the defect in a system of coordinates of the focused ion beam drawing system on the basis of the determined affine transformation and coordinate values of the selected defect to form a plurality of etched impressions near the estimated position; deriving coordinates and relative positions of the selected defect and the etched impressions by means of a visible light scattering topography; measuring coordinate values of the etched impressions by means of a focused ion beam drawing system; determining a second affine transformation on the basis of the coordinate value of the etched impressions by the focused ion beam drawing system and the coordinate values of the etched impressions by the visible light scattering topography; and estimating the position of the defect in the system of coordinates of the focused ion beam drawing system on the basis of the second affine transformation and the coordinate values of the defect by the visible light scattering topography.

According to a second aspect of the present invention, there is provided a defect-position identifying method for a semiconductor substrate comprising the steps of: forming at least three reference points on a semiconductor substrate; detecting the reference points and defects of the semiconductor substrate by means of a first evaluating system, which is provided for evaluating the defects of the semiconductor substrate, to measure coordinate values of the reference points and defects in a system of coordinates of the first evaluating system; selecting an internal defect existing in the semiconductor substrate from the detected defects; measuring coordinate values of each of the reference points by means of a marking system capable of applying a mark on the semiconductor substrate; determining an affine transformation for transforming the system of coordinates of the first evaluating system to the system of coordinates of the marking system, on the basis of the coordinate values of each of the reference points in the first evaluating system and the marking system; estimating the position of the selected defect on the marking system on the basis of the determined affine transformation and the selected defect, to form a mark near the estimated position by the marking system; and evaluating the selected defect using the formed mark by means of a second evaluating system for evaluating the defects on the semiconductor substrate.

The reference points may be impressions formed by a Vickers hardness meter.

According to a third aspect of the present invention, there is provided a defect-position identifying method for a semiconductor substrate comprising the steps of: detecting a plurality of defects of the semiconductor substrate by means of a first evaluating system, which is provided for evaluating the defects of the semiconductor substrate, to measure coordinate values of the defects; detecting at least three defects, which are not arranged on the same straight line on the semiconductor substrate, by means of a second evaluating system, which is provided for evaluating the defects of the semiconductor substrate, to measure coordinate values of the at least three defects; extracting a set of three defects forming a triangle having a shape closest to all of triangles, each of which has vertexes arranged at the defects detected by means of the second evaluating system, from the plurality of defects detected by means of the first evaluating system; and determining an affine transformation on the basis of coordinate values of the set of defects in the first evaluating defect and coordinate values of a set of defects detected by the second evaluating system.

The step of extracting the set of defects may extract a set of defects, which has a vector having a component closest to those of all of vectors connecting the defects detected by means of the second evaluating system, from the plurality of defects.

The step of extracting the set of defects may extract a set of defects forming a triangle having two sides and an angle therebetween, which are closest to two sides of each of all triangles having vertexes at the defects detected by means of the second evaluating system and an angle therebetween, respectively, from the plurality of sets of defects.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings:

FIG. 12 is an illustration for explaining the characteristics of the fourth preferred embodiment;

FIG. 14 is an illustration for explaining the characteristics of the fifth preferred embodiment;

FIG. 16 is a table for explaining an example of a system for evaluating a defect of a semiconductor substrate.

DESCRIPTION OF THE PREFERRED EMBODIMENTS

Referring now to the accompanying drawings, the preferred embodiments of the present invention will be described below.

(First Preferred Embodiment)

Figure 1:
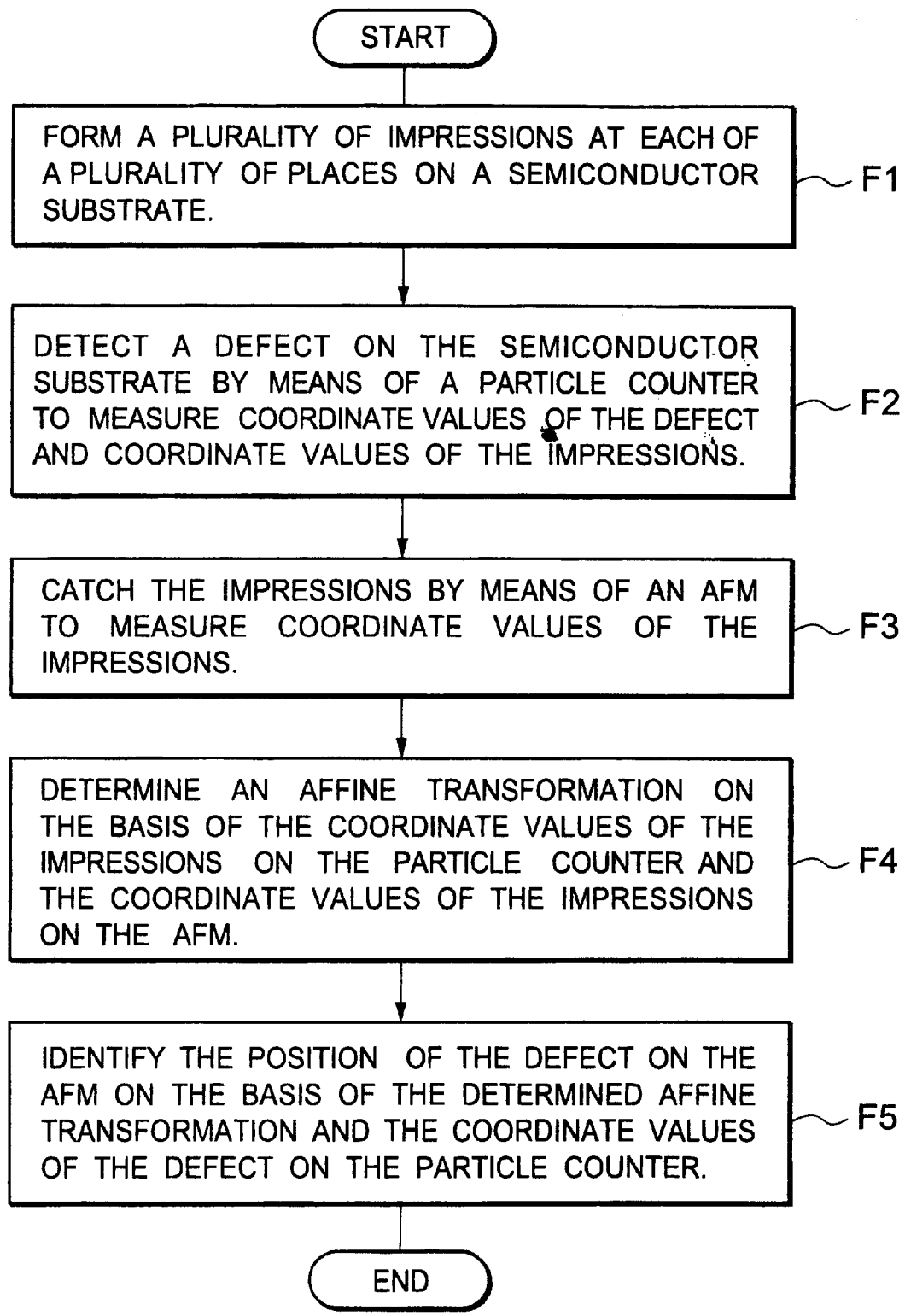
FIG. 1 is a flow chart showing a processing procedure in the first preferred embodiment of the present invention.

FIG. 1 shows a processing procedure in the first preferred embodiment of a defect-position identifying method for a semiconductor substrate according to the present invention. The defect-position identifying method in the first preferred embodiment is designed to detect a scatterer by means of a particle counter, which is capable of evaluating a foreign matter or pit on a semiconductor substrate, to observe the detected scatterer by an atomic force microscope (AFM) to deliver the coordinates of the scatterer between the particle counter and the AFM using an affine transformation.

Referring to FIG. 1, this position identifying method will be described in detail below.

Figure 2:
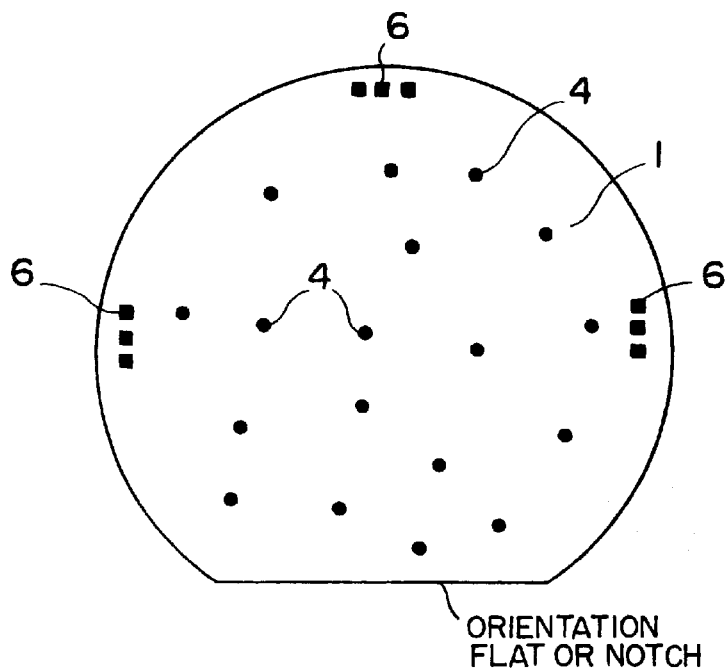
FIG. 2 is a plan view showing the surface of a semiconductor substrate for use in the first preferred embodiment.

First, three impressions are formed on a semiconductor substrate at each of three places, which are not arranged on a straight line, by means of, e.g., a Vickers hardness meter (see step F1 in FIG. 1). These impressions are used as reference points for coordinates. Each of the impressions has a size of 5 μm. By measuring the position of the center of each of the impressions, a positional precision of 1 μm can be obtained. As shown in FIG. 2, the impressions (markings) 6 are formed at a distance of about 5 mm from the periphery of the semiconductor substrate 1 so that the impressions do not obstruct the evaluation of defects 4. At each place, three impressions 6 are formed at intervals of 5 mm. This causes the impressions to be easily distinguished from other particle pits.

After the impressions are thus formed, the defects on the semiconductor substrate are detected by means of a particle counter for producing, e.g., green light having a wavelength of 488 nm, to measure the coordinate values of the defects and the coordinate values of the impressions (see step F2 in FIG. 1).

Then, the impressions on the semiconductor substrate are caught by means of an optical microscope attached to the AFM to measure the coordinate values of the impressions (see step F3 in FIG. 1).

Then, on the basis of the coordinate values of the nine (=3×3) impressions measured at step F2 and the coordinate values of the nine (=3×3) impressions measured at step F3, an affine transformation for delivering the coordinate values between the particle counter and the AFM is determined (see step F4 in FIG. 1). Assuming that the coordinates of a scatterer on the particle counter is (x, y) and the coordinates of the scatterer on the AFM is (x', y'), the affine transformation is expressed by the following formula.

$$\begin{pmatrix} x' \\ y' \end{pmatrix} = \begin{pmatrix} c_1 & c_2 \\ c_4 & c_5 \end{pmatrix} \begin{pmatrix} x \\ y \end{pmatrix} + \begin{pmatrix} c_3 \\ c_6 \end{pmatrix} \quad (1)$$

The formula (1) shows the form of a linear transformation plus a parallel translation. In a conventional method, the term for a linear translation is a rotation matrix, whereas according to the present invention, it is a general linear transformation. Therefore, the degree of freedom for the transformation is high, so that the coordinate correspondence between systems can contain a transformation which can not be expressed by only rotation, such as the extension, contraction or distortion of the system of coordinates. Thus, the correct coordinate correspondence can be expected.

In addition, coefficients $C_1$ through $C_6$ are obtained by the following formulae:

$$\begin{pmatrix} \sum_i x_i^2 & \sum_i x_i y_i & \sum_i x_i \\ \sum_i x_i y_i & \sum_i y_i^2 & \sum_i y_i \\ \sum_i x_i & \sum_i y_i & \sum_i 1 \end{pmatrix} \begin{pmatrix} c_1 \\ c_2 \\ c_3 \end{pmatrix} = \begin{pmatrix} \sum_i x_i x_i' \\ \sum_i x_i' y_i \\ \sum_i x_i' \end{pmatrix} \quad (2)$$

$$\begin{pmatrix} \sum_i x_i^2 & \sum_i x_i y_i & \sum_i x_i \\ \sum_i x_i y_i & \sum_i y_i^2 & \sum_i y_i \\ \sum_i x_i & \sum_i y_i & \sum_i 1 \end{pmatrix} \begin{pmatrix} c_4 \\ c_5 \\ c_6 \end{pmatrix} = \begin{pmatrix} \sum_i x_i y_i' \\ \sum_i y_i' y_i \\ \sum_i y_i' \end{pmatrix} \quad (3)$$

wherein $(x_i, y_i)$ are coordinates of an impression serving as a coordinate reference on the particle counter, and (xi', yi') are coordinates of the impression on the AFM. In addition, Σ means to find the sum of all of the impressions used as coordinate references. The formulae (2) and (3) determine the coefficients of the affine transformation on the basis of the method of least squares. In the conventional method, the coordinate correspondence is obtained using only two reference points, so that there is a problem in that an error in the reference points is directly reflected in the estimated result of coordinates. According to the method of the present invention, a plurality of reference points can be utilized, so that a higher precision can be expected.

Then, the formulae (2) and (3) will be derived below. With respect to coordinates $(x_i, y_i)$ of a scatterer on the particle counter and coordinates $(x_i', y_i')$ of the scatterer on the AFM, squares $R_x$ and $R_y$ of errors in x and y directions in the coordinate transformation according to the formula (1) are expressed by the following formulae.

$$R_x = \sum_i (c_1 x_i + c_2 y_i + c_3 - x_i')^2 \quad (4)$$

$$R_y = \sum_i (c_4 x_i + c_5 y_i + c_6 - y_i')^2 \quad (5)$$

In order to minimize $R_x$, the following formulae (6), (7) and (8) must be satisfied.

$$\frac{\partial R_x}{\partial c_1} = 2 \sum_i (c_1 x_i + c_2 y_i + c_3 - x_i') x_i \quad (6)$$

$$= 2 \left( c_1 \sum_i x_i^2 + c_2 \sum_i x_i y_i + c_3 \sum_i x_i - \sum_i x_i x_i' \right) = 0$$

$$\frac{\partial R_x}{\partial c_2} = 2 \sum_i (c_1 x_i + c_2 y_i + c_3 - x_i') y_i \quad (7)$$

$$= 2 \left( c_1 \sum_i x_i y_i + c_2 \sum_i y_i^2 + c_3 \sum_i y_i - \sum_i x_i' y_i \right) = 0$$

$$\frac{\partial R_x}{\partial c_3} = 2 \sum_i (c_1 x_i + c_2 y_i + c_3 - x_i') \quad (8)$$

$$= 2 \left( c_1 \sum_i x_i + c_2 \sum_i y_i + c_3 \sum_i 1 - \sum_i x_i' \right) = 0$$

By the formulae (6), (7)and(8), the formula (2) is obtained.

Similarly, by minimizing $R_y$ in the formula (5), the formula (3) is obtained.

Thus, by using the formulae (2) and (3) on the basis of the coordinate values of the measured impression, the coefficients $C_1$ through $C_6$ of the affine transformation are obtained, and the affine transformation (1) is determined.

Then, by substituting the affine transformation thus determined for the coordinate values of the defect detected by the particle counter, the position of the defect on the AFM is identified (see step F5 in FIG. 1).

Figure 3:
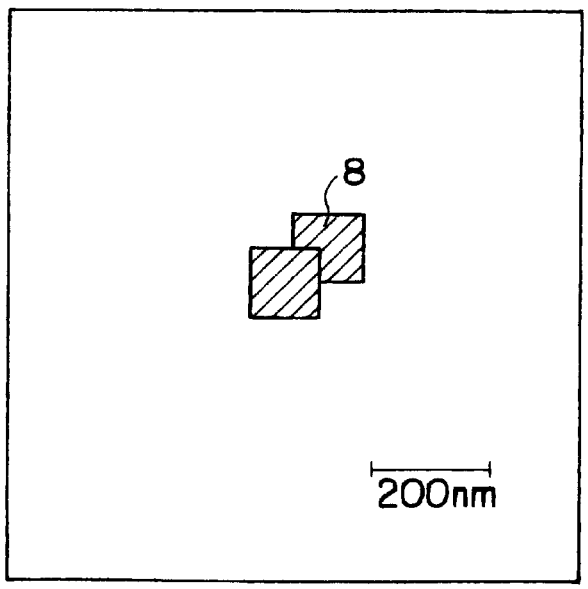
FIG. 3 is a schematic diagram showing an image of defects detected by an AFM for use in the method in the first preferred embodiment.

When the method in this preferred embodiment is actually used to evaluate a semiconductor substrate, nine examples of ten examples of scatterers on the particle counter were observed as images 8 on the AFM (see FIG. 3). When each of the defects is first caught, the scanning region of the AFM was a region of 50 μm×50 μm, and the difference from the estimated position in the formula (1) was in the range of from about 10 μm to about 20 μm. As can be seen from this preferred embodiment, by carrying out the correspondence of the system of coordinates by the affine transformation in the evaluation for the defect on the semiconductor substrate, and by using the method of least squares, it is possible to greatly improve the precision to substantially surely introduce the defect into the scanning region of the AFM.

On the other hand, in the conventional method, the origin shift and rotation angle between the X-Y stages of the particle counter and AFM are obtained by using only two impressions, to estimate the position of a scatterer on the AFM corresponding to the scatterer on the particle counter. When a defect was sought by the conventional method, an image was caught by the AFM in only one example of ten examples of scatterers on the particle counter. The scanning region of the AFM is a region of 50 μm×50 μm, so that it can be seen that errors of 50 μm or more for the coordinate correspondence in the conventional method. Thus, the correspondence of the coordinates on the particle counter to those on the AFM is insufficient by only the origin movement and rotation of the system of coordinates.

According to the method in this preferred embodiment, the delivery of coordinates between the system for macroscopically catching the defect (particle counter) and the system for microscopically catching the defect (AFM) is carried out by the affine transformation. Therefore, it is also possible to express distortion which can not be expressed by only the parallel translation and rotation of coordinates, and it is possible to more precisely identify the position of the defect than that in the conventional method.

(Second Preferred Embodiment)

Figure 4:
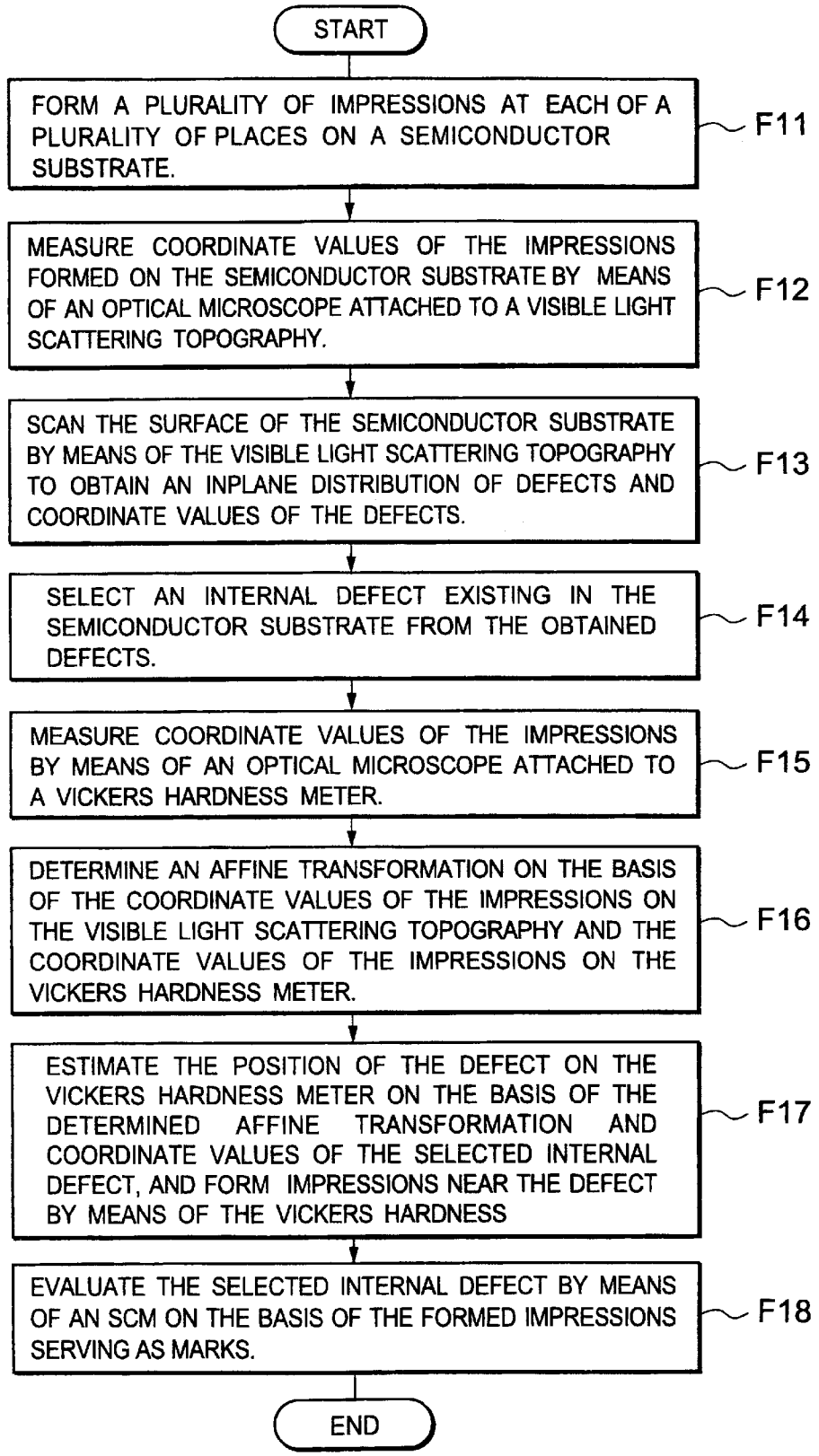
FIG. 4 is a flow chart showing a processing procedure in the second preferred embodiment of the present invention.
Figure 5:
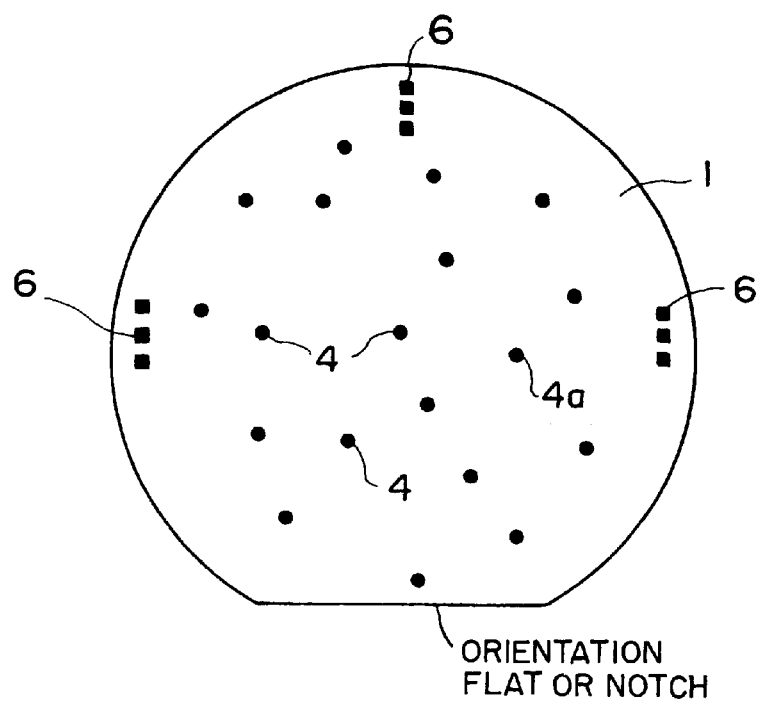
FIG. 5 is a plan view showing the surface of a semiconductor substrate for use in the second preferred embodiment.
Figure 6:
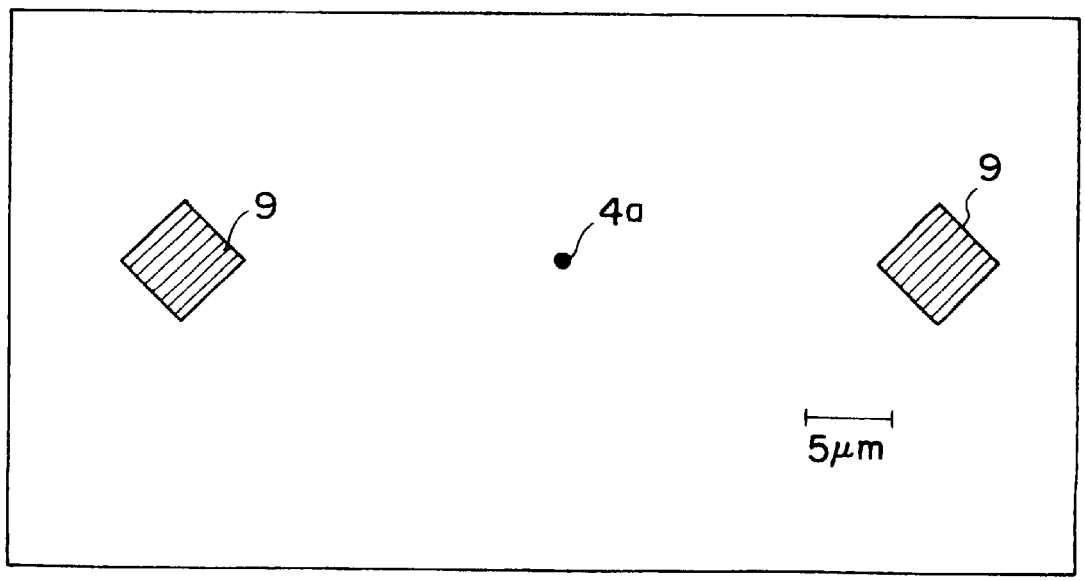
FIG. 6 is a schematic view showing the relationship between the positions of a defect and markings, the positions of which have been identified by the method in the second preferred embodiment.

Referring to FIGS. 4 through 6, the second preferred embodiment of a defect-position identifying method for a semiconductor substrate according to the present invention will be described below.

FIG. 4 is a flow chart showing a processing procedure in the second preferred embodiment of a defect-position identifying method according to the present invention. The defect-position identifying method in the second preferred embodiment is designed to identify the position of an internal defect existing in a semiconductor substrate. A visible light scattering topography is used as a system for macroscopically catching a defect, and a scanning capacitance microscope (SCM) is used as a system for microscopically catching the defect.

First, similar to the first preferred embodiment, three impressions are formed on a semiconductor substrate at each of three places, which are not arranged on a straight line, by means of, e.g., a Vickers hardness meter to be used as reference points (see step F11 in FIG. 4).

Then, the semiconductor substrate is observed by means of an optical microscope attached to a visible light scattering topography to measure the coordinate values of the impressions formed on the semiconductor substrate (see step F12 in FIG. 4). Furthermore, the reason why the impressions are caught by means of the attached optical microscope in the case of the visible light scattering topography is that the sensitivity of the visible light scattering topography is very high so that the scattered light from the impressions is too strong to measure the position.

Subsequently, the surface of the semiconductor 1, on which the impressions (markings) 6 are formed as shown in FIG. 5, is scanned by means of the visible light scanning topography to obtain an inplane distribution of defects 4 and the coordinate values of the defects (see step F13 in FIG. 4). Then, an internal defect 4a supposed to exist in the semiconductor substrate 1 is selected from the obtained defects 4 (see step F14 in FIG. 4). Furthermore, a red laser having a wavelength of 690 nm is used as incident light in the above described visible light scattering topography. By using the red laser, the incident light penetrates about 4 μm into the semiconductor substrate of, e.g., Si, from the surface thereof, so that it is possible to catch the internal defect existing in the semiconductor substrate. On the other hand, according to the first preferred embodiment, the depth of the penetration of the light into the semiconductor substrate is very shallow since the green light having a wavelength of 488 nm is used, so that it is possible to detect only foreign matters and pits on the surface of the semiconductor substrate.

Figure 15:
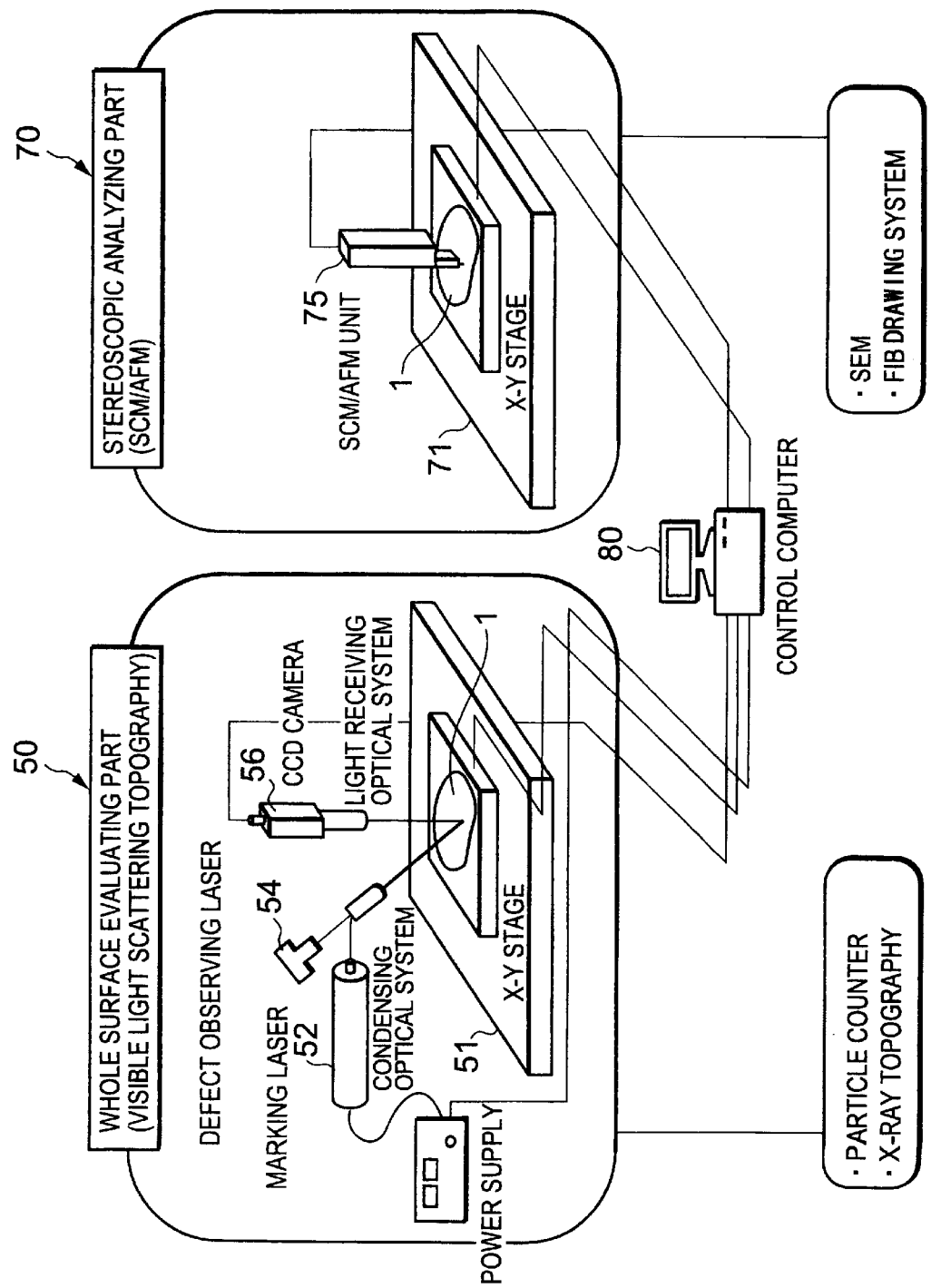
FIG. 15 is a schematic diagram showing the construction of the sixth preferred embodiment of the present invention.

Then, the semiconductor substrate is moved to the Vickers hardness meter to measure the coordinate values of the above described nine impressions by means of an optical microscope attached to the hardness meter (see step F15 in FIG. 15). Subsequently, on the basis of the coordinate values of the impressions measured at step F12 and the coordinate values of the impressions measured at step F15, an affine transformation for delivering coordinates between the visible light scattering topography and the Vickers hardness meter is determined (see step F16 in FIG. 4). This affine transformation can be determined in the same manner as that in the first preferred embodiment.

Then, on the basis of the determined affine transformation and the coordinate values of the defect selected at step F14, the position of the selected defect on the Vickers hardness meter is estimated, and impressions are formed by means of the Vickers hardness meter at a plurality of (e.g., two) positions apart from the estimated position by 20 μm (see step F17 in FIG. 4). Although the internal defect existing in the semiconductor substrate can not be caught by means of the optical microscope attached to the Vickers hardness meter, the position of the internal defect can be estimated by means of the affine transformation as described above. Furthermore, when the above described semiconductor substrate was returned to the visible light scattering topography to observe the above described defect place, it was confirmed that impressions were formed in the range of from 18 μm to 22 μm from the position of the defect. On the other hand, according to the conventional method, even if an impression was formed at a position which is very close to the estimated position of the defect and which is apart therefrom by, e.g., 20 μm, there were some cases where this impression is formed at a position apart from the actual position of the defect by 50 μm or more.

Then, the semiconductor substrate, on which the impression was formed near the defect, was evaluated by means of an SCM (see step F18 in FIG. 4). The SCM is an evaluating system for scanning a probe by the principle of the AFM to form an image of an inplane distribution of capacity of a fine MOS capacitor comprising a probe, an oxide film and a semiconductor substrate. As shown in FIG. 6, contrast of an SCM image appeared at the central portion of a region surrounded by an impression 9, and the position of the contrast was coincident with the position of a scattered image of the visible light scattering topography. In addition, no irregularity appears at the position of the defect in the AFM image obtained simultaneously with the SCM image.

Therefore, it can be seen that the internal defect 4a existing in the semiconductor substrate was caught by the SCM.

By thus using the impressions (markings) precisely formed near just by the defect at a distance of about 20 μm therefrom by the method in this preferred embodiment, it can be seen that it is possible to estimate the internal defect existing in the semiconductor substrate, which can not be observed by means of a usual optical microscope, particle counter and AFM. Furthermore, the impression 9 is an impression formed at step F17.

As described above, according to the defect-position identifying method in this preferred embodiment, it is possible to precisely identify the position of the internal defect existing in the semiconductor substrate.

(Third Preferred Embodiment)

Referring to FIGS. 7 through 10, the third preferred embodiment of a defect-position identifying method according to the present invention will be described below.

Figure 7:
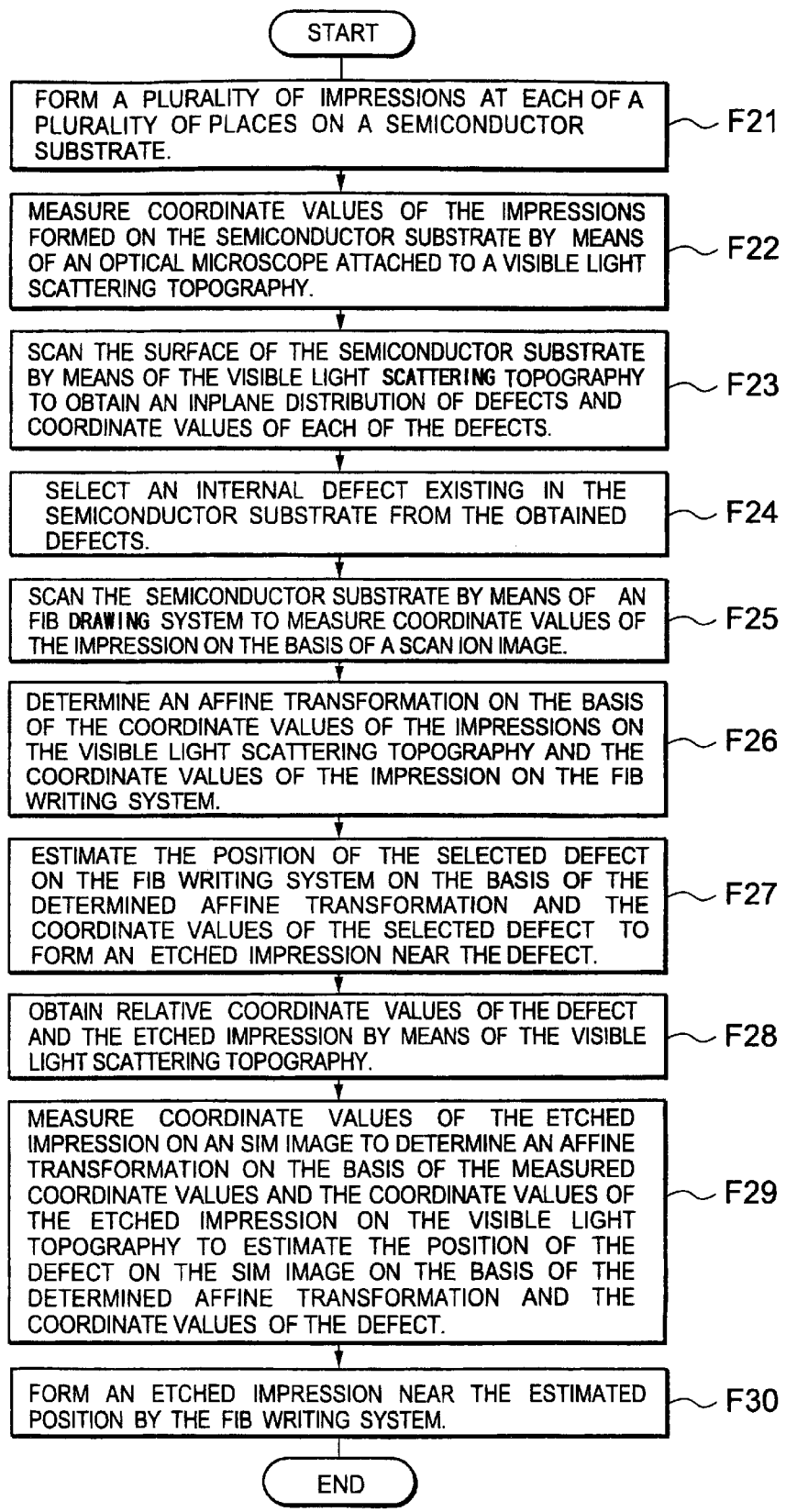
FIG. 7 is a flow chart showing a processing procedure in the third preferred embodiment of the present invention.

The processing procedure in the defect-position identifying method in the third preferred embodiment is shown in the flow cart of FIG. 7. The defect-position identifying method in the third preferred embodiment is designed to identify the position of an internal defect existing in a semiconductor substrate similar to the second preferred embodiment. Particularly, the marking precision in this preferred embodiment is better than that in the second preferred embodiment so as to directly observe the internal defect by means of the TEM.

First, similar to the second preferred embodiment, three impressions are formed on a semiconductor substrate at each of three places, which are not arranged on a straight line, by means of, e.g., a Vickers hardness meter to be used as reference points (see step F21 in FIG. 7).

Then, the semiconductor substrate is observed by means of an optical microscope attached to a visible light scattering topography to measure the coordinate values of each of the impressions (see step F22 in FIG. 7).

Subsequently, the surface of the semiconductor 1 is scanned by means of the visible light scattering topography to obtain an inplane distribution of defects and the coordinate values of the defects (see step F23 in FIG. 7). Then, an internal defect supposed to exist in the semiconductor substrate is selected from the obtained defects (see step F24 in FIG. 7).

Then, the semiconductor substrate is mounted in a focused ion beam drawing system (which will be also hereinafter referred to as an "FIB drawing system") to scan the surface of the semiconductor substrate to obtain a scanning ion microscope (which will be also hereinafter referred to as a "SIM") image to measure the coordinate values of the above described impressions on the basis of the SIM image (see step F25 in FIG. 7). Subsequently, on the basis of the coordinate values of the impressions measured at step F22 and the coordinate values of the impressions measured at step F25, an affine transformation for delivering the coordinates between the visible light scattering topography and the FIB drawing system is determined (see step F26 in FIG. 7). Furthermore, the affine transformation can be determined in the same manner as that in the second preferred embodiment.

Figure 8:
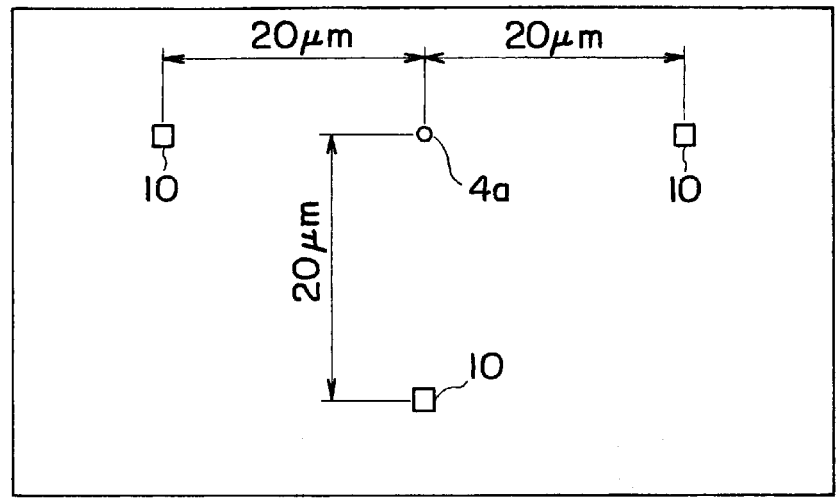
FIG. 8 is a schematic view showing the relationship between the positions of a defect and markings, the positions of which have been identified by the method in the third preferred embodiment.

Then, on the basis of the determined affine transformation and the coordinate values of the defect selected at step F24, the position of the selected defect on the FIB drawing system is estimated, and a plurality of impressions (markings) 10 (three impressions in FIG. 8) are formed, by etching using the FIB drawing system, at positions apart from the estimated position 4a by 20 μm as shown in FIG. 8 (see step F27 in FIG. 7). Although the internal defects in the semiconductor substrate can not appear on the SIM image of the FIB drawing system, the positions of the internal defects can be estimated on the basis of the coordinate values of the impressions as described above.

Figure 9:
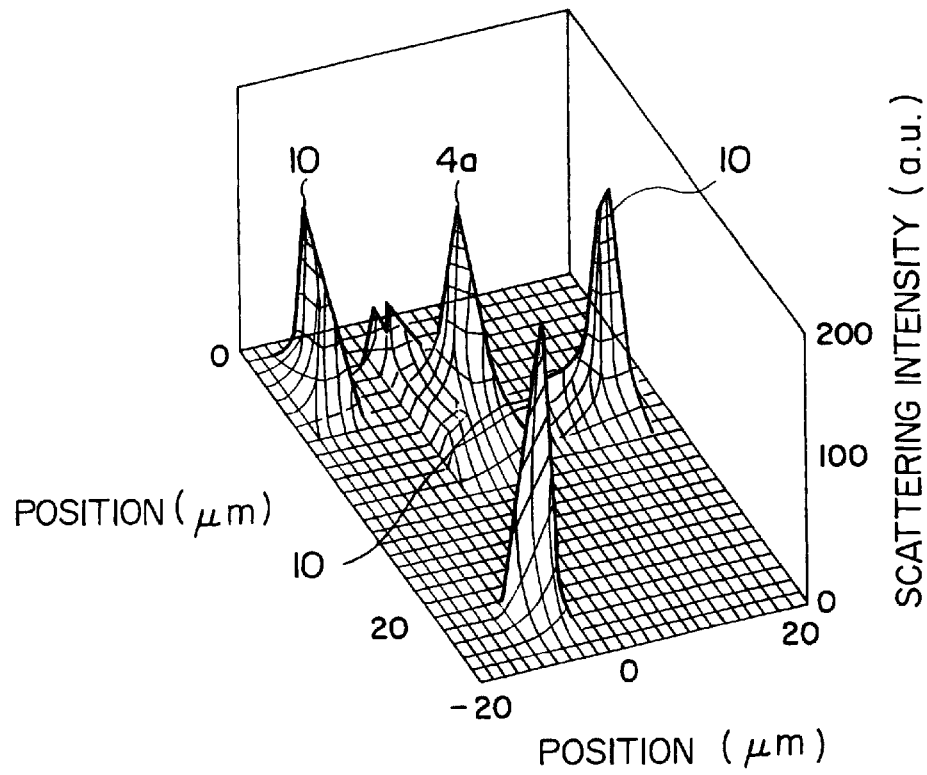
FIG. 9 is an illustration for explaining a method for precisely obtaining the relationship between the relative positions of a defect and markings.
Figure 10:
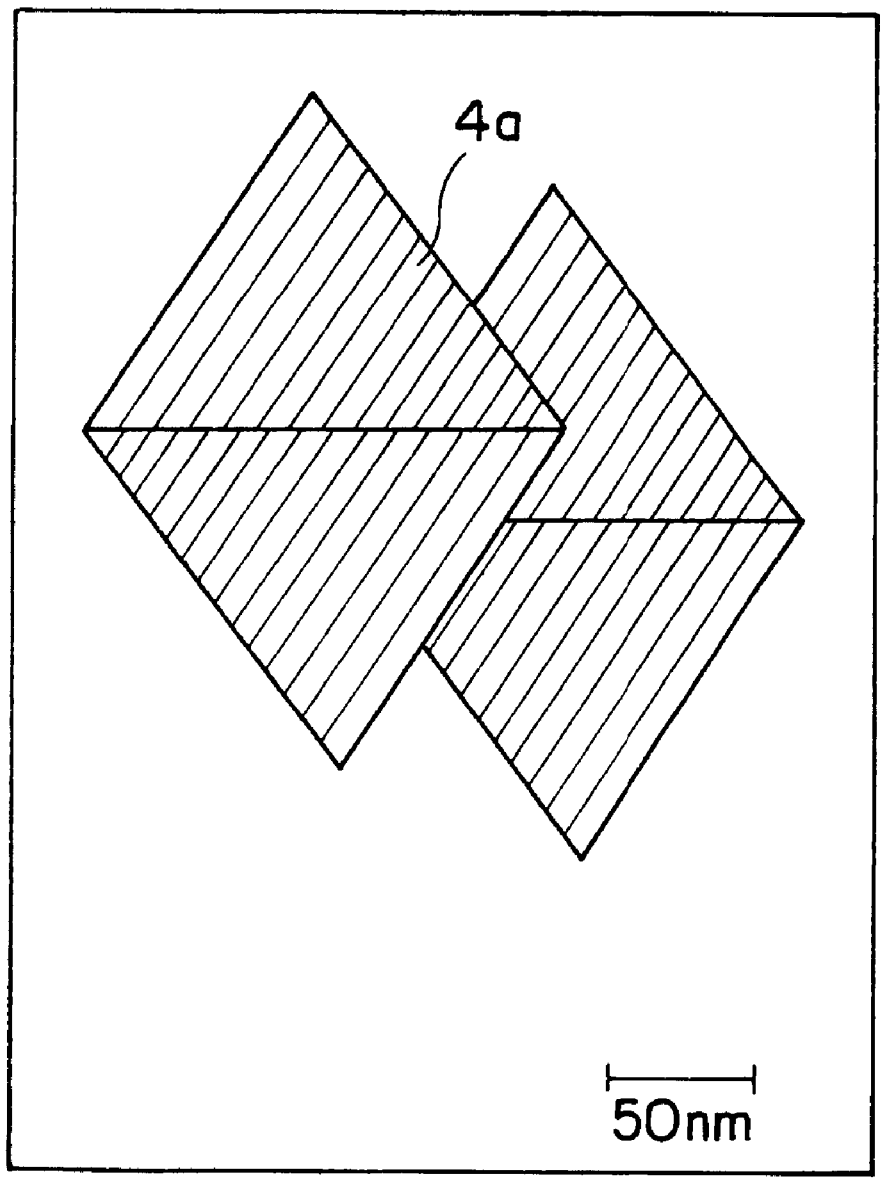
FIG. 10 is a schematic diagram showing an image of defects caught by a TEM.

Then, the semiconductor substrate is evaluated by the visible light scattering topography again to derive relative coordinate values of the above described defect 4a from the etched impressions 10 (see step F28 in FIG. 7). The size of the impression etched by the FIB drawing system in this preferred embodiment was about 200 μm which was smaller than the wavelength of the light. Therefore, in this preferred embodiment, the power of the laser was adjusted to cause the defect 4a and the etched impression to be as small as possible, to obtain a scattered image. The image of the scatterer (defect or the like) has a point symmetric light intensity distribution. Therefore, as shown in FIG. 9, a light intensity was measured for each pixel of the image on the basis of the scattered image, and the relative positions of the defect 4a and the etched impression were obtained with a precision of 0.1 μm by calculating the position of the center of gravity of each scattered image.

Then, the semiconductor substrate is mounted on the stage of the FIB drawing system to measure the coordinates of the etched impressions 10 on the SIM image as shown at step 29 in FIG. 7. Then, a new affine transformation is determined on the basis of the measured coordinate values and the coordinate values of the etched impressions obtained at step F28, and the position of the defect on the SIM image is estimated on the basis of the newly determined affine transformation and the coordinate values of the defect (see step F29 in FIG. 7). Then, etched impressions (markings) are newly formed at a distance of 5 μm from the estimated position by means of the FIB drawing system (see step F30 in FIG. 7).

When evaluation was carried out again by means of the visible light scattering topography for confirmation, the error of position between the FIB etched impression formed at a distance of 5 μm and the defect was not greater than 0.1 μm. Therefore, when a cross-section TEM sample having a thickness of about 0.2 μm was worked between the FIB etched impressions, a defect image was caught by means of the TEM (see FIG. 10).

As the distance between the marking and the defect decreases, the magnification of the SIM image can be increased, so that the precision of the position can be improved. In this preferred embodiment, it was possible to finally form the marking at a distance of 5 μm from the defect, so that it was possible to improve the precision of the position.

As described above, according to the defect-position identifying method in this preferred embodiment, it is possible to precisely identify the position of the defect.

(Fourth Preferred Embodiment)

Figure 11:
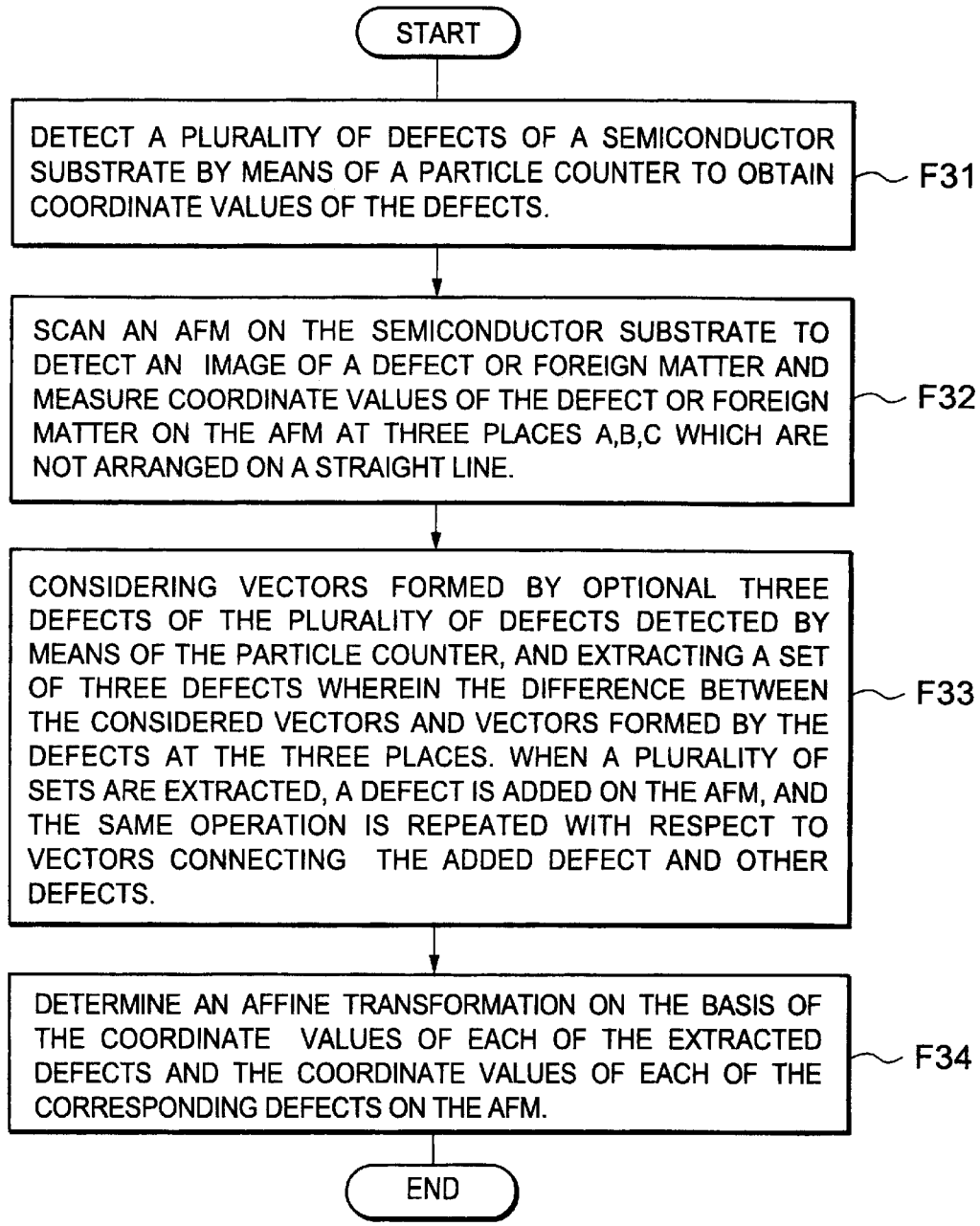
FIG. 11 is a flow chart showing the fourth preferred embodiment of a processing procedure according to the present invention.

Referring to FIGS. 11 and 12, the fourth preferred embodiment of a defect-position identifying method for a semiconductor substrate according to the present invention will be described below.

The flow chart of FIG. 11 shows a processing procedure in the fourth preferred embodiment of a defect-position identifying method according to the present invention. The defect-position identifying method in the forth preferred embodiment can carry out the correspondence between the systems of coordinates of a system for macroscopically catching a defect and a system for microscopically catching the defect, without the need of any markings to stereoscopically analyze a defect.

First, as shown at step F31 in FIG. 11, a plurality of (three or more) defects on a semiconductor substrate are detected by means of a particle counter to measure the coordinate values of these defects.

Then, an atomic force microscope (AFM) is scanned on the semiconductor substrate to detect an image of a defect or foreign matter to measure the coordinate values of the image. This is carried out for each of three places, which are not arranged on a straight line (see step F32 in FIG. 11). In this case, assuming that the images detected at the three places are A, B and C, three vectors AB, BC and CB can be obtained.

Therefore, a set of three defects A', B' and C' are extracted so that the distances between the three vectors A'B', B'C' and C'A', which are made by optional three defects A', B' and C' of a plurality of defects previously detected by means of the particle counter at step F31, and the above described corresponding three vectors AB, BC and CA are minimum (see step F33 in FIG. 11). This will be described below.

First, considering only points A and B. Then, a combination wherein the difference between a vector formed by optional two points on the particle counter and a vector connecting the point A with the point B is not greater than a certain threshold (the difference between components x and y is 100 $\mu$m or less in this preferred embodiment) is extracted, and assuming that proposals for the points A and B are A' and B', respectively. Then, considering a point C. Then, a point C', at which the difference between a vector connecting proposals A' and B' for the extracted points A and B and a vector connecting AC and BC is not greater than a threshold, is extracted.

When a plurality of proposals exist, a reference point D is additionally provided as shown in, e.g., FIG. 12. Then, considering vectors connecting other reference points A, B and C with the point D serving as a starting point, a combination wherein the difference between the proposals for the corresponding vectors is not greater than a threshold is extracted. This operation is repeated several times, so that a scatterer on the particle counter corresponding to the defect or foreign matter detected by means of the AFM is substantially uniquely determined.

According to the conventional method, scatterers estimated to approximate to each other are selected as references. Therefore, the correspondence of a defect or foreign matter on the particle counter to another defect or foreign matter on the AFM is often carried out. In this case, a great error occurs in the correspondence for the system of coordinates, so that it is difficult to come within the range of the AFM. According to the method in this preferred embodiment, the correspondence of the same defect or foreign matter between the AFM and the particle counter is surely carried out.

Then, an affine transformation is determined on the basis of the coordinate values of each of the extracted defects and the coordinate value of a defect on a corresponding AFM (see step F34 in FIG. 11).

By using the affine transformation thus determined, the system of coordinates on the particle counter can precisely correspond to the system of coordinates on the AFM.

After the method in this preferred embodiment was actually carried out, nine examples of ten examples of scatterers on the particle counter were caught when the scanning region of the AFM was a region of 20 $\mu$m×20 $\mu$m. In addition, the differences between the estimated positions of the scatterers on the AFM and the actual positions were in the range of from about 5 $\mu$m to about 10 $\mu$m.

As described above, according to this preferred embodiment, it is possible to precisely determine the position of the defect.

(Fifth Preferred Embodiment)

Figure 13:
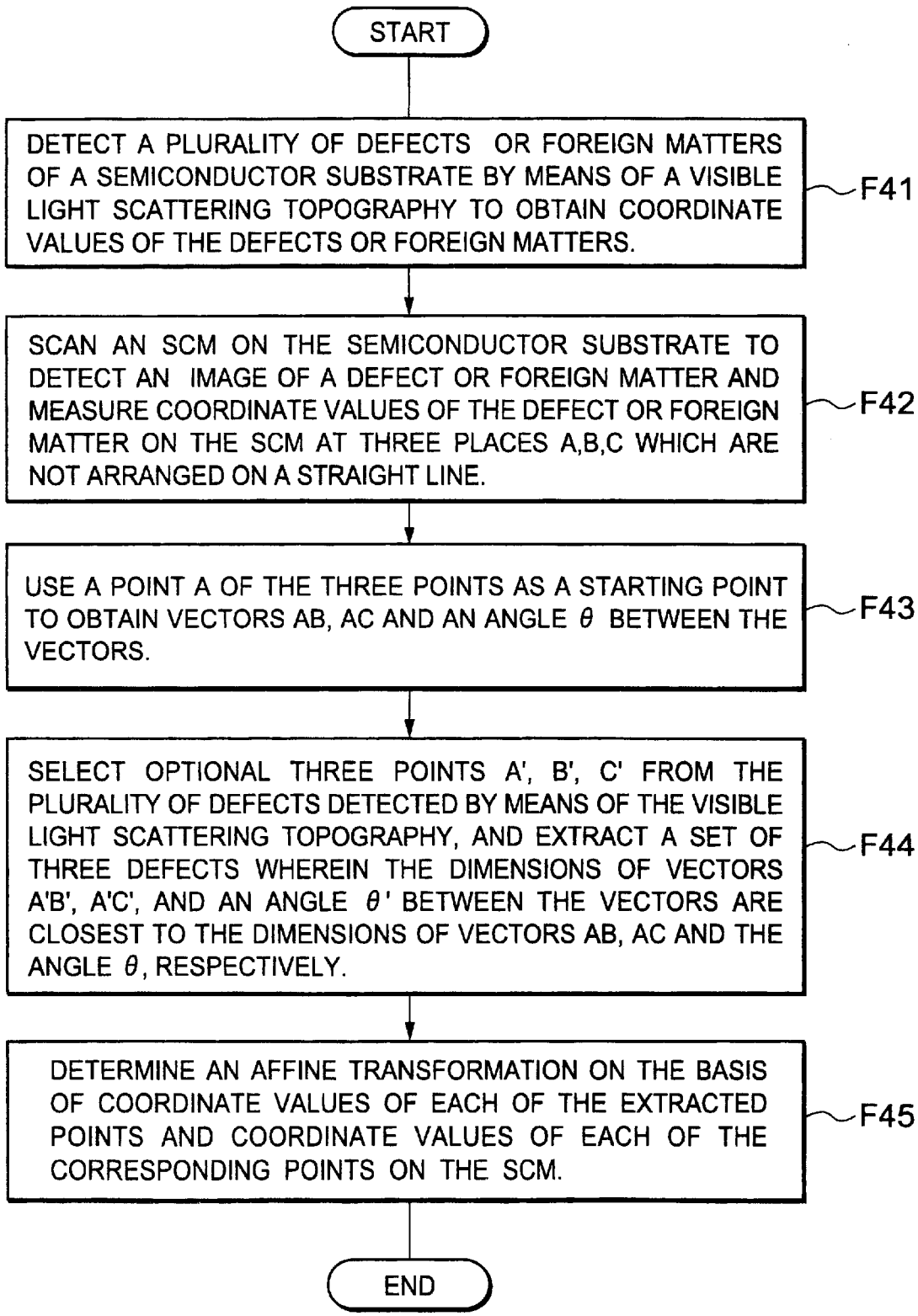
FIG. 13 is a flow chart showing a processing procedure in the fifth preferred embodiment of the present invention.

Referring to FIGS. 13 and 14, the fifth preferred embodiment of a defect-position identifying method for a semiconductor substrate according to the present invention will be described below.

The flow chart of FIG. 13 shows a processing procedure in the fifth preferred embodiment of a defect-position identifying method according to the present invention. The defect-position identifying method in the fifth preferred embodiment is designed to identify an internal defect in a semiconductor substrate. Similar to the fourth preferred embodiment, the defect-position identifying method in the fifth preferred embodiment can carry out the correspondence between the systems of coordinates on a system for macroscopically catching a defect (a visible light scattering topography) and a system for microscopically catching the defect (an SCM), without the need of any markings to stereoscopically analyze the defect. Furthermore, the fourth preferred embodiment takes notice of vectors formed by defects considering the defects as points, whereas this preferred embodiment takes notice of two sides and an angle therebetween.

First, as shown at step F41 in FIG. 13, the whole surface of a semiconductor substrate is evaluated by means of a visible light scattering topography to detect at least three defects or foreign matters to measure the coordinate values of these defects or foreign matters.

Then, a scanning capacitance microscope (SCM) is scanned on the semiconductor substrate to detect an image of a defect or foreign matter to measure the coordinate values of the image. This is carried out for each of three places, which are not arranged on a straight line (see step F42 in FIG. 13).

Assuming that the images of the defects or foreign matters detected at the three places are points A, B and C, vectors AB and AC from the point A serving as a starting point, and an angle $\theta$ between these vectors are derived (see step F43 in FIG. 13).

Then, optional three defects or foreign matters A', B' and C' are selected from a plurality of defects or foreign matters detected by means of the visible light scattering topography at step F41, and a set of three defects A', B' and C' are extracted so that vectors A'B' and A'C' and an angle $\theta$ between the vectors A'B' and A'C' are closest to the above described vectors AB and AC and the angle $\theta$, respectively (see step F44 in FIG. 13). This will be described below.

With respect to optional three points on the visible light scattering topography, considering vectors connecting one point serving as a starting point with other two points. The lengths of the vectors and the angle between the vectors are obtained, and a combination wherein the differences from the lengths and angles in the case of the points A, B, C are not greater than certain thresholds (the difference between the lengths is 100 $\mu$m or less, and the difference between the angles is 0.1° or less in this preferred embodiment) is extracted to be used as proposals for the points A, B and C. When a plurality of proposals exist, an additional reference point is prepared to consider vectors connecting the additional reference point serving as a starting point with other reference points A', B' and C', and a corresponding combination of scatterers is extracted similarly from the scatterers on the visible light scattering topography. This operation is repeated several times, so that a scatterer on the visible light scattering topography corresponding to the defect or foreign matter detected by means of the SCM is substantially uniquely determined (see FIG. 14).

Then, similar to the first preferred embodiment, an affine transformation is determined on the basis of the coordinate values of each point on the SCM corresponding to the coordinate values of each of the extracted points (see step F45 in FIG. 13).

By using the affine transformation thus determined, the correspondence of the systems of coordinates between the visible light scattering topography and the SCM can be precisely carried out.

After the method in this preferred embodiment was actually carried out, three examples of ten examples of scatterers on the visible light scattering topography were caught by means of the SCM when the scanning region of the SCM was a region of 20 μm×20 μm, and the error from the center of the scanning region was about 10 μm. It is considered that the reason why the remaining seven examples were not caught by means of the SCM is that the defects were positioned at greater depths than the depth detected by means of the SCM (about 0.3 μm). In the conventional method, errors due to incorrect corresponding points and errors due to the coordinate correspondence considering only the origin shift and the rotation angle of the system of coordinates are added, so that it is difficult to introduce the defects into the visual field of the SCM. Therefore, it is not possible to determine whether the reason why no detection is carried out by means of the SCM is that the coordinate shift occurs or the defect is positioned at a deep place.

As described above, according to this preferred embodiment, it is possible to precisely the position of the defect.

(Sixth Preferred Embodiment)

Referring to FIG. 15, the sixth preferred embodiment of the present invention will be described below.

The sixth preferred embodiment relates to a defect-position identifying system for a semiconductor substrate according to the present invention, and the construction thereof is shown in FIG. 15. This preferred embodiment is shown by a combination of a visible light scattering topography system 50 and an SCM/AFM system 70. First, when a semiconductor substrate 1 is set on an X-Y stage 51 of a visible light scattering topography 50, markings are automatically formed at three places on the peripheral portion of the semiconductor substrate 1 by means of a laser marking mechanism 52 built in the visible light scattering topography 50, similar to the second preferred embodiment. Then, the visible light scattering topography 50 scans on the semiconductor substrate 1 to obtain the whole surface map of defects and the coordinate values of the markings. Then, when the semiconductor substrate 1 is set on an X-Y stage 71 of the SCM/AFM system 70, the coordinates of a laser marking are measured by means of an optical microscope attached to a unit 75. on the basis of the coordinates of the markings on the visible light topography 50 and the coordinates of the markings on the stereoscopic analyzing system 70, an affine transformation expressed by the formula (1) is determined by means of a control computer 80, and the coordinate correspondence is carried out using the affine transformation. When a desired scatterer is selected by the map on the visible light scattering topography 50, the coordinates on the stereoscopic analyzing system 70 are calculated by the control computer 80 to automatically obtain the coordinates of a target defect on the SCM and AFM.

When the semiconductor substrate 1 is set on the visible light scattering topography 50 again, the coordinates of the formed markings are measured again, and the system of coordinates when the whole surface of the semiconductor substrate is first evaluated, is reproduced using the affine transformation expressed by the formula (1). Thus, when desired scatterer on the visible light scattering topography is selected, markings can be always formed around the defect by means of the laser marking mechanism 52 to be used for the TEM analysis.

As described in the fourth or fifth preferred embodiment, this preferred embodiment also has the function of automatically extracting a scatterer on the visible light scattering topography corresponding to the defect or foreign matter observed by means of the SCM/AFM to carry out the coordinate correspondence without the need of any markings.

In this preferred embodiment, the whole surface evaluating part is separated from the stereoscopic analyzing part. Therefore, the whole surface evaluating part can be combined with other systems, such as a particle counter and an X-ray topography, and the stereoscopic analyzing part can be combined with other systems, such as a scanning electron microscope (SEM) and an FIB drawing system.

Furthermore, while the coordinate transformation has been carried out using a linear expression of x and y in the above described first through sixth preferred embodiments, a coordinate transformation using a formula including quadratic terms of x and y will be described below.

$$x'=a_1x^2+a_2xy+a_3y^2+a_4x+a_5y+a_6$$

$$y'=b_1x^2+b_2xy+b_3y^2+b_4x+b_5y+b_6 \qquad (9)$$

Three impressions at each of six places, i.e., 18 impressions in total, were formed on a semiconductor substrate, and the coordinates of the respective impressions were measured by means of a particle counter and an optical microscope attached to an AFM. The coefficients a1 through a6 and b1 through b6 in the formula (9) were determined on the basis of the measured results, and the position of a scatterer on the AFM corresponding to that on the particle counter was estimated by the formula (9). As a result, nine examples of ten examples were observed as AFM images. With respect to the observed AFM images, the shift from the estimated position in the formula (9) was in the range of from 10 μm to 20 μm.

Then, the semiconductor substrate was used to carry out the coordinate transformation using the formula (1). As a result, nine examples of ten examples were observed as AFM images, and the shift from the formula (1) was in the range of from 10 μm to 20 μm. This result means that even if the formula (9) including quadratic terms as the coordinate transformation is used, the positional precision is substantially the same as that in the formula (1) including linear terms or less. That is, the actual coordinate transformation between the systems has only to be the affine transformation, and it is not required to incorporate high-order terms.

As described above, according to the present invention, the position of the defect on the semiconductor substrate can be precisely identified.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. A defect-position identifying method for a semiconductor substrate comprising the steps of:

forming at least three reference points on a semiconductor substrate;

detecting said reference points and a defect on said semiconductor substrate by means of a first evaluating system, which is provided for evaluating said defect on said semiconductor substrate, to measure coordinate values of said reference points and said defect in a system of coordinates of said first evaluating system;

detecting said reference points on said semiconductor substrate by means of a second evaluating system, which is provided for evaluating said defect on said semiconductor substrate, to measure coordinate values of said reference points in a system of coordinates of said second evaluating system;

determining an affine transformation for transforming said system of coordinates of said first evaluating system to said system of coordinates of said second evaluating system on the basis of said coordinate values of each of said reference points in said first and second evaluating systems; and identifying the position of said defect in said system of coordinates of said second evaluating system on the basis of the determined affine transformation and said coordinate values of said defect in said system of coordinates of said first evaluating system.

2. A defect-position identifying method for a semiconductor substrate as set forth in claim 1, wherein said reference points are impressions formed by a Vickers hardness meter.

3. A defect-position identifying method for a semiconductor substrate as set forth in claim 1, wherein said first evaluating system is a particle counter, and said second evaluating system comprises an optical microscope and an atomic force microscope having a common system of coordinates to said optical microscope, said coordinate values of said reference points in said system of coordinates of said second evaluating system being measured by means of said optical microscope.

4. A defect-position identifying method for a semiconductor substrate as set forth in claim 3, wherein said reference points are impressions formed by a Vickers hardness meter.

5. A defect-position identifying method for a semiconductor substrate as set forth in claim 1, wherein said first evaluating system comprises an optical microscope and a visible light scattering topography having a common system of coordinates to said optical microscope, and said second evaluating system comprises a focused ion beam drawing system, said coordinate values of said reference points and said defect in said system of coordinates of said first evaluating system being measured by means of said optical microscope and said visible light scattering topography.

6. A defect-position identifying method for a semiconductor substrate as set forth in claim 5, wherein said reference points are impressions formed by a Vickers hardness meter.

7. A defect-position identifying method for a semiconductor substrate as set forth in claim 5, which further comprises a step of selecting an internal defect existing in said semiconductor substrate from said defects detected by means of said visible light scattering topography, and wherein said step of identifying said position of said defect in said system of coordinates of said second evaluating system comprises the steps of:

estimating the position of said defect in a system of coordinates of said focused ion beam drawing system on the basis of said determined affine transformation and coordinate values of the selected defect to form a plurality of etched impressions near the estimated position;

deriving coordinates and relative positions of said selected defect and said etched impressions by means of a visible light scattering topography;

measuring coordinate values of said etched impressions by means of a focused ion beam drawing system;

determining a second affine transformation on the basis of said coordinate value of said etched impressions by said focused ion beam drawing system and said coordinate values of said etched impressions by said visible light scattering topography; and estimating the position of said defect in said system of coordinates of said focused ion beam drawing system on the basis of said second affine transformation and said coordinate values of said defect by said visible light scattering topography.

8. A defect-position identifying method for a semiconductor substrate as set forth in claim 7, wherein said reference points are impressions formed by a Vickers hardness meter.

9. A defect-position identifying method for a semiconductor substrate comprising the steps of:

forming at least three reference points on a semiconductor substrate;

detecting said reference points and defects of said semiconductor substrate by means of a first evaluating system, which is provided for evaluating said defects of said semiconductor substrate, to measure coordinate values of said reference points and defects in a system of coordinates of said first evaluating system;

selecting an internal defect existing in said semiconductor substrate from the detected defects;

measuring coordinate values of each of said reference points by means of a marking system capable of applying a mark on said semiconductor substrate;

determining an affine transformation for transforming said system of coordinates of said first evaluating system to said system of coordinates of said marking system, on the basis of said coordinate values of each of said reference points in said first evaluating system and said marking system;

estimating the position of the selected defect on said marking system on the basis of the determined affine transformation and the selected defect, to form a mark near the estimated position by said marking system; and evaluating the selected defect using the formed mark by means of a second evaluating system for evaluating said defects on said semiconductor substrate.

10. A defect-position identifying method for a semiconductor substrate as set forth in claim 9, wherein said reference points are impressions formed by a Vickers hardness meter.

11. A defect-position identifying method for a semiconductor substrate comprising the steps of:

detecting a plurality of defects of said semiconductor substrate by means of a first evaluating system, which is provided for evaluating said defects of said semiconductor substrate, to measure coordinate values of said defects;

detecting at least three defects, which are not arranged on the same straight line on said semiconductor substrate, by means of a second evaluating system, which is provided for evaluating said defects of said semiconductor substrate, to measure coordinate values of said at least three defects;

extracting a set of three defects forming a triangle having a shape closest to all of triangles, each of which has vertexes arranged at said defects detected by means of said second evaluating system, from said plurality of defects detected by means of said first evaluating system; and determining an affine transformation on the basis of coordinate values of said set of defects in said first evaluating defect and coordinate values of a set of defects detected by said second evaluating system.

12. A defect-position identifying method for a semiconductor substrate as set forth in claim 11, wherein said step of extracting said set of defects extracts a set of defects, which has a vector having a component closest to those of all of vectors connecting said defects detected by means of said second evaluating system, from said plurality of defects.

13. A defect-position identifying method for a semiconductor substrate as set forth in claim 11, wherein said step of extracting said set of defects extracts a set of defects forming a triangle having two sides and an angle therebetween, which are closest to two sides of each of all triangles having vertexes at said defects detected by means of said second evaluating system and an angle therebetween, respectively, from said plurality of sets of defects.

* * * * *